United States Patent
Strehlow et al.

(10) Patent No.: US 12,096,991 B2
(45) Date of Patent: *Sep. 24, 2024

(54) POSITION DETERMINING DEVICE FOR DETERMINING THE POSITION OF AN OBJECT WITHIN A TUBULAR STRUCTURE

(71) Applicant: Fraunhofer-Gesellschaft zur Foerderung der angewandten Forschung e.V., Munich (DE)

(72) Inventors: Jan Strehlow, Bremen (DE); Torben Pätz, Bremen (DE); Horst Hahn, Bremen (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 99 days.

This patent is subject to a terminal disclaimer.

(21) Appl. No.: 16/756,118

(22) PCT Filed: Apr. 11, 2019

(86) PCT No.: PCT/EP2019/059266
§ 371 (c)(1),
(2) Date: Apr. 15, 2020

(87) PCT Pub. No.: WO2019/197534
PCT Pub. Date: Oct. 17, 2019

(65) Prior Publication Data
US 2021/0369350 A1    Dec. 2, 2021

(30) Foreign Application Priority Data
Apr. 11, 2018 (DE) ............ 10 2018 108 643.1

(51) Int. Cl.
A61B 34/20 (2016.01)

(52) U.S. Cl.
CPC ...... *A61B 34/20* (2016.02); *A61B 2034/2055* (2016.02); *A61B 2034/2061* (2016.02)

(58) Field of Classification Search
CPC ......... A61B 34/20; A61B 34/00; A61B 5/066; A61B 5/7246; A61B 2034/2055; A61B 2034/2061; A61B 2562/0266
See application file for complete search history.

(56) References Cited

U.S. PATENT DOCUMENTS

| | | | |
|---|---|---|---|
| 10,586,338 B2 | 3/2020 | Ekin | |
| 2013/0172739 A1* | 7/2013 | Paladini | A61B 6/5247 601/2 |

(Continued)

FOREIGN PATENT DOCUMENTS

| CN | 104936516 A | 9/2015 |
|---|---|---|
| CN | 105979899 A | 9/2016 |

(Continued)

OTHER PUBLICATIONS

International Search Report (+ English translation) and Written Opinion of the International Searching Authority completed Jun. 27, 2019, in International Patent Application No. PCT/EP2019/059266, 13 pages.

(Continued)

*Primary Examiner* — Amelie R Davis
(74) *Attorney, Agent, or Firm* — Lowe Graham Jones PLLC; Ellen M. Bierman

(57) ABSTRACT

The invention relates to a position determining device for determining a position of an elongate object within a tubular structure, said position determining device comprising a first providing unit for providing a first distribution of curvature values at a plurality of first points along a path within the tubular structure. The position determining device further comprises a second providing unit for providing a second distribution of strain values or of curvature values at a (Continued)

plurality of points along the object, and a position determining unit for determining the position of the object relative to the path on the basis of the first and second distributions.

16 Claims, 9 Drawing Sheets

(56) References Cited

U.S. PATENT DOCUMENTS

| | | |
|---|---|---|
| 2013/0287280 A1 | 10/2013 | Ekin et al. |
| 2013/0303892 A1 | 11/2013 | Zhao et al. |
| 2014/0336501 A1 | 11/2014 | Masumoto |
| 2015/0254526 A1 | 9/2015 | Denissen |
| 2016/0077651 A1 | 3/2016 | Na et al. |
| 2016/0302690 A1 | 10/2016 | Nebuya et al. |
| 2016/0302869 A1 | 10/2016 | Chopra |

FOREIGN PATENT DOCUMENTS

| | | |
|---|---|---|
| CN | 106999130 A | 8/2017 |
| CN | 110022786 A | 7/2019 |
| DE | 10 2016 119 579 | 4/2018 |
| JP | 2011-189074 A | 9/2011 |
| JP | 2013-150650 | 8/2013 |
| JP | 2014213124 | 11/2014 |
| JP | 2016-502412 | 1/2016 |
| JP | 2016-508399 | 3/2016 |
| JP | 2016523596 | 8/2016 |
| JP | 2017502728 | 1/2017 |
| JP | 2017-531388 A | 10/2017 |
| WO | 2005/084571 | 9/2005 |
| WO | 2012088535 A1 | 6/2012 |
| WO | 2014/028400 | 2/2014 |
| WO | 2014/053925 | 4/2014 |
| WO | 2014191262 | 12/2014 |
| WO | 2015/089013 | 6/2015 |
| WO | 2018/069462 | 4/2018 |

OTHER PUBLICATIONS

International Search Report and Written Opinion of the International Searching Authority completed Dec. 8, 2017, in International Patent Application No. PCT/EP2017/076101, 11 pages.

Office Action and Search Report by China National Intellectual Property Administration issued on Aug. 2, 2023 in Chinese Patent Application No. 201980035183.1, 12 pages.

Office Action issued in Chinese Application No. 201980035183.1 by the Chinese National Intellectual Property Administration on Dec. 27, 2023.

* cited by examiner p

POSITION DETERMINING DEVICE FOR DETERMINING THE POSITION OF AN OBJECT WITHIN A TUBULAR STRUCTURE

CROSS-REFERENCE TO RELATED APPLICATIONS

This application is a U.S. National Phase of International Patent Application No. PCT/EP2019/059266, filed Apr. 11, 2019; which claims the benefit of priority from Germany Patent Application No. 10 2018 108 643.1, filed Apr. 11, 2018, the contents of which applications are incorporated herein by reference in their entireties.

TECHNICAL FIELD

The invention relates to a position determining device, a method and a computer program for determining the position of an elongate object, in particular of a medical instrument such as a catheter, a bronchoscope or a guide wire, within a tubular structure, for example the blood vessels or the respiratory tract. The invention also relates to an imaging system that includes the position determining device, and also to an imaging method and an imaging computer program.

BACKGROUND

Position determining devices that use tracking techniques based on electromagnetic (EM) or optical shape sensing (OSS) to determine the position of an interventional instrument inside a patient's body are known in medical applications. Optical shape sensing is typically performed by analysing a plurality of optical curvature sensors, which for their part are constructed of strain sensors arranged concentrically around the fibre cross-section. However, these EM and OSS tracking techniques can be relatively inaccurate due to inhomogeneities of the EM field, for example, or errors in the interpolation and integration of curvature information.

BRIEF DESCRIPTION OF THE DRAWINGS

Embodiments of the invention shall now be described with reference to the attached Figures, in which.

DETAILED DESCRIPTION

Figure 1:
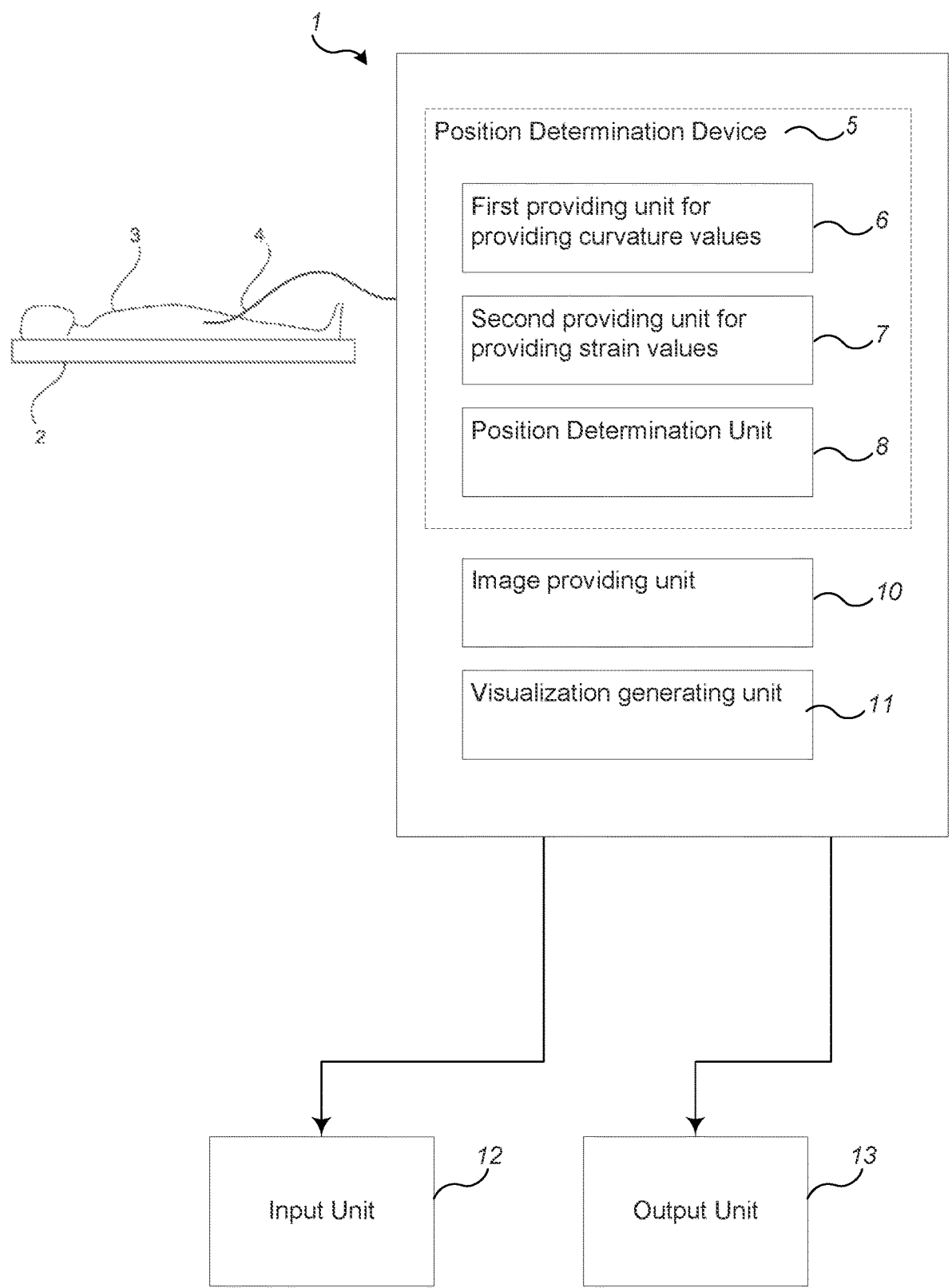
FIG. 1 shows an embodiment of an imaging system in schematic form.

An object of the present invention is to provide a position determining device, a method and a computer program that allows the position of an elongate object within a tubular structure to be better determined. Another object of the present invention is to provide an imaging system that includes the positioning device, as well as an imaging method and an imaging computer program.

The object is achieved by a position determining device for determining the position of an elongate object, in particular of a medical instrument, within a tubular structure, said position determining device comprising:

a first providing unit for providing a first distribution of curvature values at a plurality of first points along a path within the tubular structure, a second providing unit for providing a second distribution of strain values or curvature values at a plurality of second points along the object, a position determining unit for determining the position of the object relative to the path on the basis of the first and second distributions.

The curvature values of the first distribution at the plurality of first points along the tubular structure and the strain values or curvature values of the second distribution at the plurality of second points along the object are local values. By determining the position of the object within the tubular structure on the basis of this local information and not on the basis of global information, it is possible to improve significantly the accuracy with which the position is determined, as this method is less sensitive to measurement errors. For example, the accuracy with which the position is determined may be less susceptible to global measurement errors such as drift, field inhomogeneities, etc., and in particular may be completely unsusceptible. The position of the object can also be determined without it being necessary, for example, to reconstruct the shape of the object on the basis of the curvature values of the second distribution.

The first providing unit may be a storage unit in which the curvature values of the first distribution are stored, and the first providing unit may be capable of providing the stored curvature values of the first distribution. However, the first providing unit may also be a receiver unit for receiving the curvature values of the first distribution from a first determining unit, for example, and for providing the received curvature values of the first distribution. Furthermore, the first providing unit may itself be the first determining unit. The second providing unit, too, may be a storage unit or a receiver unit. The second providing unit may also be a second determining unit.

The curvature values of the first distribution are preferably specified. They may have been determined on the basis of an image of the tubular structure, for example a computed tomography image, a magnetic resonance imaging image or some other image. The curvature values of the first distribution can also be determined in some other way. For example, in a previous method, one or more curvature sensors can be moved within the tubular structure so that they are at known first points within the tubular structure, while the curvatures of the tubular structure are measured using the curvature sensors. Another way of generating the curvature values is to simulate the position of the medical object within the tubular structure extracted from the image data.

The tubular structure can be, for example, a blood vessel system, a respiratory system, or some other branched tubular structure. The tubular structure can also be an engineered tubular structure, for example a pipeline system, a tunnel system, a cable duct system, etc. . . . The object is preferably a medical instrument such as a guide wire, a catheter, or a bronchoscope. However, the object can also be a nonmedical object that is moved, for example, within a pipeline system, a tunnel system, a cable duct system, etc.

In one preferred embodiment, the curvature values of the first distribution and the second distribution are scalar. The position of the object within the tubular structure can therefore be determined without using directional curvature information. In one embodiment, two local curvatures in two different directions can be determined at a respective point, for example in the transverse and vertical axis directions, and these two local curvatures can be combined to form a scalar curvature value that is indicative of the local curvature at the respective point. A scalar mean curvature value or a scalar Gaussian total curvature value can be determined, for example. However, the curvature values can also be vector values. For example, the two local curvatures, such as the curvature relative to the vertical axis and the curvature relative to the transverse axis, can be viewed as the two-component curvature values at the respective point.

It is preferred that the first providing unit is adapted to provide a scalar distribution of curvature values along a path within the tubular structure as the first distribution. The second providing unit is preferably then adapted to provide a distribution of scalar strain values at the plurality of second points along the object as the second distribution, so that the position determining unit determines the position of the object relative to the path on the basis of the scalar curvature values of the first distribution and the scalar strain values of the second distribution. As only scalar strain values are needed in this situation, a relatively small amount of technical effort is necessary to determine the position of the object within the tubular structure.

It is further preferred that the second providing unit is adapted to determine the second distribution on the basis of optical signals from optical strain sensors arranged along the object. The optical strain sensors are preferably integrated in one single-core optical fibre. There is preferably only one strain sensor at each point along the object. This allows the second distribution of scalar strain values to be determined with a technical effort that is further reduced in comparison with curvature sensors and which can also be relatively easy for the user to handle.

If, in another embodiment, the second distribution is a distribution of curvature values, these can be determined by means of OSS curvature sensors, for example, or by groups of EM or RFID sensors. The relative position in relation to other sensors within the group of sensors is sufficient for this group of EM or RFID sensors to calculate the local curvatures.

The first providing unit is preferably adapted a) to apply a dissimilarity measure to the first distribution and the second distribution for different possible candidate positions of the object relative to the path, wherein the dissimilarity measure is adapted to return a dissimilarity score indicative of a dissimilarity of the two distributions in the respective candidate position for each candidate position of the object relative to the path, and b) to determine the position of the object relative to the path on the basis of the dissimilarity scores determined for the different candidate positions. In one embodiment, the position determining unit is adapted to specify the candidate position for which the smallest dissimilarity score has been determined as the position of the object relative to the path. This by itself may result in the position of the object relative to the path being determined relatively accurately.

The position determining device is preferably adapted, in addition, to provide a plurality of first distributions of curvature values for a plurality of paths within the tubular structure that result from branching of the structure, wherein the position determining unit is adapted to determine the position of the object relative to one of said paths on the basis of the first distributions and the second distribution. The position determining unit is adapted, in particular, a) to determine for each path a distribution of dissimilarity scores for different candidate positions of the object relative to the respective path and b) to determine the position of the object relative to one of the paths on the basis of the dissimilarity scores determined for the different paths and different candidate positions. This can result in the position of the object relative to one of the paths being accurately determined if the tubular structure has a plurality of possible paths where the object could be.

It is also preferred that the second providing unit is adapted to provide a plurality of second distributions along the object for different points in time, wherein the plurality of second distributions correspond to a plurality of positions of the object relative to a path within the tubular structure, wherein the position determining unit is adapted a) to determine for each path and for each point in time a distribution of dissimilarity scores for different candidate positions of the object relative to the respective path, and b) to determine the positions of the object relative to one of the paths on the basis of the dissimilarity scores determined for the different paths, the different points in time and the different candidate positions. The dissimilarity scores determined for the different points in time and the different candidate positions can be interpreted, in particular, as a map, wherein a respective dissimilarity score is entered in the map for different locations specified by the respective points in time and candidate positions, wherein the position determining unit is adapted a) to provide a route measure which returns a route score for a route through the respective map that ends at a candidate position for a latest point in time and begins at a candidate position for an earlier point in time, said route score depending on the dissimilarity scores along the respective route, b) to determine for each path a route through the respective map by means of the route measure, for which a minimum route score is determined such that a respective optimal route is calculated for different paths and thus for different maps, and c) to determine positions of the object relative to one of the paths on the basis of optimal routes calculated for the different paths by taking into account the route scores determined for said optimal routes. The position determining device is preferably adapted to provide a route measure which includes a component that becomes greater as the sum of the dissimilarity scores increases along the respective route. In one embodiment, the position determining unit is adapted to specify the positions defined by the route with the lowest route score of all the optimal routes as the positions of the object relative to one of the paths. This can produce a further improvement in determining the position of the object within the tubular structure.

However, it is also preferred that the position determining unit is adapted a) to calculate optimal routes for different points in time such that a respective optimal route with a corresponding route score is determined for different points in time and different paths, wherein, in order to determine an optimal route with a corresponding route score for a path and a particular point in time, use is made of the dissimilarity scores calculated for the particular point in time and for earlier points in time and for the candidate positions, which can be interpreted as a map for the respective route and the particular point in time, b) to select at each point in time, from the calculated optimal routes, the optimal route for which a minimum route score has been determined, wherein the route score is increased, before the optimal route with the minimum route score is selected, for an optimal route for which no minimum route score was determined at earlier points in time compared to the route scores determined for the other optimal routes, and c) to specify the positions defined by the selected optimal route as the positions of the object relative to one of the paths. This can produce a further improvement in the accuracy with which the position of the object within the tubular structure is determined.

The position determining unit can be adapted to apply the dissimilarity measure by a) determining a spatial first gradient distribution of the first distribution, b) determining a spatial second gradient distribution of the second distribution, c) comparing, for each location along the object, the respective gradient of the second distribution with the respective curvature gradients of the first distribution, wherein the respective candidate position defines which respective gradient of the second distribution is compared with which respective curvature gradient of the first distribution at the respective location, wherein, for the respective location and for the respective candidate position, a sub-dissimilarity measure is applied which is dependent a) on the directions of the gradients relative to each other and/or b) on the absolute value of the gradient of the first distribution and the absolute value of the gradient of the second distribution, wherein a sub-dissimilarity score is determined for each location by applying the sub-dissimilarity measure, and d) summing the sub-dissimilarity scores determined for a candidate position, in order to determine a respective dissimilarity score for the respective candidate position. In one embodiment, the value of the sub-dissimilarity measure decreases with increasing similarity of the directions of the two gradients relative to each other. This decrease can be monotonic and/or continuous. In one embodiment, the sub-dissimilarity measure also returns a first score when the absolute value of the gradient of the first distribution is less than a first absolute value threshold and the absolute value of the gradient of the second distribution is less than a second absolute value threshold, and a second score when the absolute value of the gradient of the first distribution is not less than the first absolute value threshold and/or the absolute value of the gradient of the second distribution is not less than the second absolute value threshold, the first score being less than the second score. The sub-dissimilarity measure may also include both components, that is, a first component that returns a score which decreases with increasing similarity of the gradients, and a second component that returns a score which is lower when the absolute value of the gradient of the first distribution is less than the first absolute value threshold and the absolute value of the gradient of the second distribution is less than the second absolute value threshold, and otherwise returns a higher score. The first component and the second component can be linearly combined, for example, which also includes simple addition. These two components can also be combined nonlinearly. In one embodiment, the two components are combined multiplicatively. The result of this combination is a scalar score for the sub-dissimilarity measure.

In another embodiment, the score returned for the sub-dissimilarity measure decreases with decreasing absolute value of the gradients of the first and second distribution. This means that said score decreases when both of the absolute values of the two gradients decrease. This decrease can be monotonic and/or continuous. Said score can also be combined linearly or nonlinearly with the score returned for the aforementioned first component. For example, said score can be multiplied by the score of the aforementioned first component, or the scores can be added.

However, the position determining unit may also be adapted to apply the dissimilarity measure by a) determining local maxima of the first distribution, b) determining local maxima of the second distribution, c) assigning a local maximum of the second distribution to each local maximum of the first distribution, so that the sum of all the spatial distances between assigned local maxima is minimal, wherein each local maximum of the second distribution is assigned to only one local maximum of the first distribution, and d) adding the spatial distances between the assigned local maxima of the first distribution and the assigned local maxima of the second distribution. Furthermore, the position determining unit may be adapted to apply the dissimilarity measure by a) comparing the respective value of the second distribution with the respective value of the first distribution for each location along the object, wherein the respective candidate position defines which respective value of the second distribution is compared with which respective value of the first distribution at the respective location, wherein, for the respective location and for the respective candidate position, a sub-dissimilarity measure is used which is zero if i) the respective value of the first distribution is above a predefined first threshold or ii) the respective value of the first distribution is below the first threshold and the respective value of the second distribution is below a predefined second threshold, and which otherwise has a positive value, and b) summing the sub-dissimilarity scores determined for a candidate position, in order to determine a respective dissimilarity score for the respective candidate position. It has been found that applying these dissimilarity measures can produce a further improvement in determining the position of the object in the tubular structure. However, other dissimilarity measures can also be applied, of course.

The position determining unit can also be adapted to apply the dissimilarity measure by applying a cross-correlation, in particular a normalised cross-correlation, to the first distribution and the second distribution for the respective candidate position. The position determining unit is adapted, in particular, to calculate the arithmetic mean $E_D$ of the strain values or curvature values of the second distribution, the arithmetic mean $E_T$ of the curvature values of the first distribution, the standard deviation $\sigma_D$ of the strain values or curvature values of the second distribution, the standard deviation $\sigma_T$ of the curvature values of the first distribution and finally the normalised cross-correlation by using the following equation:

$$\frac{1}{n}\Sigma_i \frac{1}{\sigma_D \sigma_T}(D(i) - E_D)(T(i) - E_T),$$

where n is the number of curvature values of the first distribution and the number of strain values or curvature values of the second distribution, the i index indicating the individual curvature values of the first distribution and the individual strain values or curvature values of the second distribution, where D(i) denotes the respective strain value or curvature value of the second distribution and T(i) denotes the respective curvature value of the first distribution. The strain value or curvature value D(i) of the second distribution and the curvature value T(i) of the first distribution are the respective i-th values that are coincident at the respective candidate position. Given that the first distribution and the second distribution are displaced differently relative to each other for different candidate positions, different first points of the first distribution and different second points of the second distribution overlap for different candidate positions, which also means in general that different strain or curvature values of the second distribution and curvature values of the first distribution are coincident and that different normalised cross-relations result for different candidate positions. It has been found that applying this dissimilarity measure based on a normalised cross-relation can produce a further improvement in determining the position of the object in the tubular structure.

The aforementioned object is achieved by an imaging system, said imaging system comprising:
- a position determining device for determining the position of an elongate object within a tubular structure in accordance with claim 1,
- an imaging unit for providing an image of the tubular structure,
- a visualisation generating unit for generating a visualisation of the tubular structure on the basis of the image provided and the position determined.

The aforementioned object is also achieved by a position determining method, said method comprising the steps of:
- a first providing unit providing a first distribution of curvature values at a plurality of first points along a path within the tubular structure,
- a second providing unit providing a second distribution of strain values or curvature values at a plurality of second points along the object,
- a position determining unit determining the position of the object relative to the path on the basis of the first and second distributions.

The aforementioned object is also achieved by an imaging method, said imaging method comprising the steps of:
- an imaging unit providing an image of a tubular structure,
- a position determining device according to claim 1 determining the position of an elongate object within the tubular structure, and
- a visualisation generating unit generating a visualisation of the tubular structure on the basis of the image provided and the position determined.

The aforementioned object is also achieved by a computer program for determining the position of an elongate object, wherein the computer program includes program code means adapted to cause the position determining device according to claim 1 to carry out the position determining method according to claim 15 when it is executed on the position determining device.

The aforementioned object is also achieved by an imaging computer program comprising program code means for causing an imaging system according to claim 12 to carry out the imaging method according to claim 13 when the computer program is executed on the imaging system.

It should be understood that the position determining device according to claim 1, the imaging system according to claim 12, the position determining method according to claim 15, the imaging method according to claim 13, the computer program according to claim 16 and the imaging computer program according to claim 14 have similar and/or identical embodiments, as defined in particular in the dependent claims.

FIG. 1 shows, in schematic form and by way of example, an embodiment of an imaging system 1 comprising a position determining device 5 for determining the position of an instrument 4 within a tubular structure, an imaging unit 10 for providing an image of the tubular structure and a visualisation generating unit 11 for generating a visualisation of the tubular structure on the basis of the image provided and the position determined. In this embodiment, the tubular structure is a vascular structure of a patient 3 who is lying on an examination table 2. Position determining device 5 includes a first providing unit 6 for providing curvature values indicative of curvatures of the tubular structure at a plurality of first points along the tubular structure, said first providing unit 6 in this embodiment being capable of determining the curvature values on the basis of the image provided by imaging unit 10. Imaging unit 10 is able, in particular, to provide a three-dimensional image of the tubular structure, for example a computed tomography image or a magnetic resonance imaging image, which may have been obtained before insertion of instrument 4 into patient 3, i.e. the image provided can be a three-dimensional, pre-interventional image. The first providing unit 6 may be capable of segmenting the tubular structure within the provided image, and determining the curvature values on the basis of this segmentation of the tubular structure in the image. These curvature values are local curvature values and form a first distribution.

In this embodiment, instrument 4 is a catheter which has optical strain sensors at a plurality of second points along catheter 4. Position determining device 5 includes a second providing unit 7 for providing strain values on the basis of optical signals received from the strain sensors. The strain values are scalar and indicative of the extensions at the respective second points and for that reason are local strain values.

Position determining device 5 also includes a position determining unit 8 for determining the position of instrument 4 within the tubular structure on the basis of the first curvature values and the second strain values. In this embodiment, these first and second values are scalar. In particular, two local curvatures of the tubular structure can be determined at a respective point in two different directions, and these two local curvatures can be combined to form a scalar curvature value that is indicative of the local curvature at the respective spatial point. A scalar mean curvature value can be calculated using the following equation, for example:

$$K_m = 1/2 \cdot (k_1 + k_2) \tag{1}$$

where $K_m$ is the scalar mean curvature value and $k_1$, $k_2$ are the local curvatures in the two different directions. A (Gaussian) curvature value $K_t$ can also be calculated using the following equation:

$$K_t = k_1 k_2 \tag{2}$$

The variables $k_1$ and $k_2$ can be viewed as the primary curvatures of the tubular structure, for example, i.e. the eigenvalues of the shape operator of the tubular structure at the respective point.

Position determining unit 8 is adapted to apply a dissimilarity measure to the first distribution and the second distribution for different possible candidate positions of catheter 4 object relative to the path, wherein the dissimilarity measure is adapted to return a dissimilarity score indicative of a dissimilarity of the two distributions in the respective candidate positions for each candidate position of catheter 4 relative to the path. Position determining unit 8 is also adapted to determine the position of catheter 4 relative to the path on the basis of the dissimilarity scores determined for the different candidate positions. Position determining unit 8 may be adapted, for example, to specify the candidate position for which the smallest dissimilarity score has been determined as the position of catheter 4 relative to the path.

The position determining device is also adapted to determine the position of catheter 4 in the tubular structure even when the tubular structure has a plurality of paths. More particularly, the first providing unit 6 is adapted to provide a plurality of first distributions of curvature values for a plurality of paths within the tubular structure, wherein position determining unit 8 is adapted to determine the position of catheter 4 relative to one of said paths on the basis of the first distributions and the second distribution. Position determining unit 8 is preferably adapted to determine for each path a distribution of dissimilarity scores for different candidate positions of catheter 4 relative to the respective path and to determine the position of catheter 4 relative to one of the paths on the basis of the dissimilarity scores determined for the different paths and different candidate positions.

In addition, the second providing unit 7 is adapted to provide a plurality of second distributions along catheter 4 for different points in time, wherein the plurality of second distributions correspond to a plurality of positions of catheter 4 relative to a path within the tubular structure. Position determining unit 8 is adapted to determine, for each path and for each point in time, a distribution of dissimilarity scores for different candidate positions of the medical instruments relative to the respective path, and to determine the positions of catheter 4 relative to one of the paths on the basis of the dissimilarity scores determined for the different paths, the different points in time and different candidate positions. In particular, the dissimilarity scores determined for the different points in time and the different candidate positions can be interpreted as a map, wherein a respective dissimilarity score is entered in the map for different locations specified by the respective points in time and candidate positions. Position determining unit 8 is then adapted to provide a route measure which returns a route score for a route through the respective map that ends at a candidate position for a latest point in time and begins at a candidate position for an earlier point in time, said route score depending on the dissimilarity scores along the respective route, Position determining unit 8 is also adapted to determine for each path a route through the respective map by means of the route measure, for which a minimum route score is determined such that a respective optimal route is calculated for different paths. Furthermore, position determining unit 8 is adapted to determine the positions of catheter 4 relative to one of the paths on the basis of optimal routes calculated for the different paths by taking into account the route scores determined for said optimal routes.

Position determining unit 8 is adapted, in particular, to provide a route measure that becomes greater as the sum of the dissimilarity scores increases along the respective route. In addition, position determining unit 8 is preferably adapted to specify determine the positions defined by the route with the lowest route score of all the optimal routes as the position of catheter 4 relative to one of the paths.

It is also preferable that position determining unit 8 is adapted to calculate optimal routes for different points in time such that a respective optimal route with a corresponding route score is determined for different points in time and different paths, wherein, in order to determine an optimal route with a corresponding route score for a path and a particular point in time, use is made of the dissimilarity scores calculated for the particular point in time and for earlier points in time and for the candidate positions, which can be interpreted as a map for the respective route and the particular point in time. Position determining unit 8 is preferably adapted, in addition, to select at each point in time, from the calculated optimal routes, the optimal route for which a minimum route score has been determined, wherein the route score is increased, before the optimal route with the minimum route score is selected, for an optimal route for which no minimum route score was determined at earlier points in time compared to the route scores determined for the other optimal routes. Position determining unit 8 is preferably adapted, furthermore, to specify the positions defined by the selected optimal route as the positions of the catheter 4 relative to one of the paths.

In order to determine a dissimilarity score, position determining unit 8 can be adapted to calculate gradients of the measured strain sensor profile and gradients of the curvature profile of the tubular structure. Position determining unit 8 can thus be adapted to apply the dissimilarity measure by determining a spatial first gradient distribution of the first distribution and a spatial second gradient distribution of the second distribution. Position determining unit 8 is then also adapted to compare, for each location along the object, the respective gradient of the second distribution with the respective curvature gradients of the first distribution, wherein the respective candidate position defines which respective gradient of the second distribution is compared with which respective curvature gradient of the first distribution at the respective location and wherein, for the respective location and for the respective candidate position, a sub-dissimilarity measure is applied which decreases with increasing similarity of the directions of the gradients relative to each other. This decrease with increasing similarity may be monotonic, for example. Alternatively or additionally, the sub-dissimilarity measure can return a lower score when the absolute value of the gradient of the first distribution is less than a predefined first absolute value threshold and the absolute value of the gradient of the second distribution is less than a predefined second absolute value threshold, and otherwise returns a higher score. That means that the sub-dissimilarity measure has at least one or at least two components, wherein a first component returns a score that decreases with increasing similarity of the gradient directions, and/or wherein a second component returns a score that is lower when the absolute value of the gradient of the first distribution is less than a predefined first absolute value threshold and the absolute value of the gradient of the second distribution is less than a predefined second absolute value threshold, and otherwise returns a higher score. That means that, for all corresponding gradient values, a penalty term is calculated that is high when a) both gradients show in dissimilar directions and/or b) neither of the two gradients is small, and whether the respective gradient value is small or not is determined by comparing it with a respective absolute value threshold.

By applying the sub-dissimilarity measure, a sub-dissimilarity score is determined for each location. Position determining unit 8 is also adapted to sum the sub-dissimilarity scores determined for a candidate position in order to determine a respective dissimilarity score for the respective candidate position. That means, in other words, that the sum of all the penalty terms is a measure for the degree to which the strain sensor profile matches the curvature profile.

Position determining unit 8 can also be adapted to apply a different dissimilarity measure, by determining local maxima of the first distribution and local maxima of the second distribution. That means that position determining unit 8 can be adapted to find all the local maxima in the strain sensor profile and the curvature profile. Position determining 8 is then adapted further to assign a local maximum of the second distribution to each local maximum of the first distribution, so that the sum of all the spatial distances between assigned local maxima is minimal, wherein each local maximum of the second distribution is assigned to only one local maximum of the first distribution. To that end, position determining unit 8 can be adapted to apply a brute-force approach to assignment. Position determining unit 8 is then adapted further to add the spatial distances between the assigned local maxima of the first distribution and the assigned local maxima of the second distribution, so as to calculate a dissimilarity score.

However, position determining unit 8 can also be adapted to apply the dissimilarity measure by comparing the respective value of the second distribution with the respective value of the first distribution for each location along catheter 4, wherein the respective candidate position defines which respective value of the second distribution is compared with which respective value of the first distribution at the respective location, wherein, for the respective location and for the respective candidate position, a sub-dissimilarity measure is used which is zero if a) the respective value of the first distribution is above a predefined first threshold or b) the respective value of the first distribution is below the first threshold and the respective value of the second distribution is below a predefined second threshold, and which otherwise returns a positive value. This is based on the observation that zero curvatures in the first distribution result in corresponding zeros in the measured extensions. This dissimilarity measure can also be viewed as injective mapping of zeros, where a binary convolution between small curvatures and small strain values is calculated. The sub-dissimilarity scores determined for a candidate position are summed, in turn, in order to determine a respective dissimilarity score for the respective candidate position.

Position determining unit 8 can also be adapted to apply the dissimilarity measure by applying a cross-correlation, in particular a normalised cross-correlation, to the first distribution and the second distribution for the respective candidate position. More particularly, position determining unit 8 can be adapted to calculate the arithmetic mean $E_D$ of the strain values of the second distribution, the arithmetic mean $E_T$ of the curvature values of the first distribution, the standard deviation $\sigma_D$ of said strain values, the standard deviation $\sigma_T$ of said curvature values and finally the normalised cross-relation by using the following equation:

$$\frac{1}{n}\Sigma_i \frac{1}{\sigma_D \sigma_T}(D(i) - E_D)(T(i) - E_T),$$

where n is the number of curvature values and thus, in this example, also the number of strain values, wherein the i index indicates the individual curvature value and the individual strain values, wherein D(i) indicates the respective strain value and T(i) indicates the respective curvature value. The strain value D(i) and the curvature value T(i) are the respective i-th values that are coincident at the respective candidate position. Given that the first distribution and the second distribution are displaced differently relative to each other for different candidate positions, different first points of the first distribution and different second points of the second distribution overlap for different candidate positions, which also means in general that different strain values and curvature values are coincident and that different normalised cross-relations result for different candidate positions. In this example, the dissimilarity measure is the normalised cross-relation or depends on it.

Visualisation generating unit 11 is able to generate the visualisation of the tubular structure on the basis of the image provided and the determined position of instrument 4 within the tubular structure, such that the determined position of instrument 4 is visualised in the provided image, or in a further image derived from the image provided by the imaging unit and showing the desired structures inside the patient. Imaging system 1 also includes an output unit 13, such as a display for displaying the visualisation to a user, and an input unit 12, such as a keyboard, a computer mouse, a touchpad, etc., so during the time that instrument 4 is within the tubular structure of patient 3, the user can see where exactly instrument 4 is located within the tubular structure, which is a help for the user when using instrument 4 inside the patient. For example, instrument 4 may have detection and/or treatment characteristics, and the visualisation displayed can support the user when carrying out detection and/or treatment procedures by displaying on output unit 13 the exact position of the tip of instrument 4, for example, relative to the tubular structure.

Figure 2:
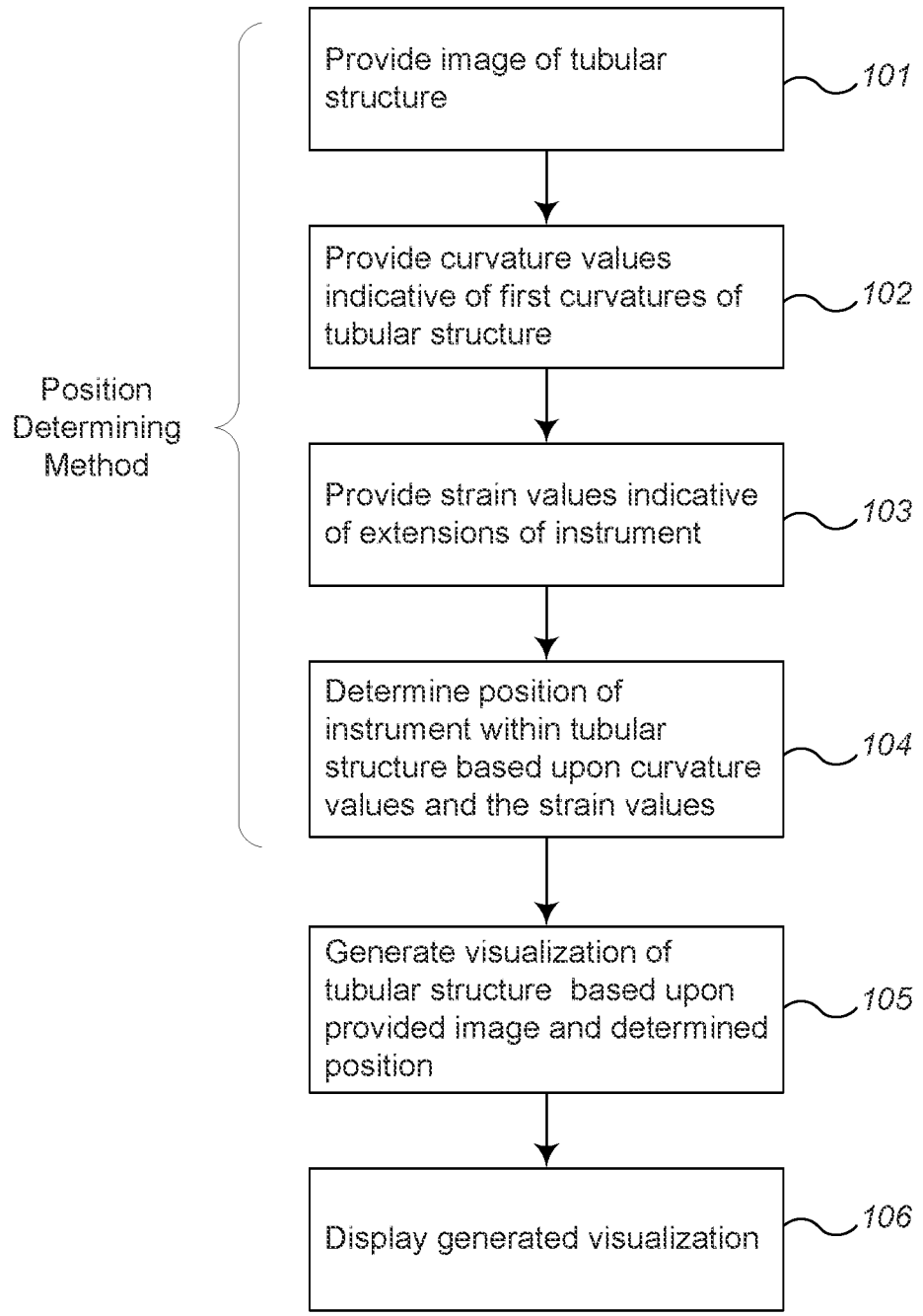
FIG. 2 shows a flow diagram representing an embodiment of an imaging method.

In the following, an embodiment of an imaging process shall be described by way of example with reference to the flow diagram shown in FIG. 2.

In step 101, an image of the tubular structure is provided by imaging unit 10, and in step 102, the curvature values indicative of curvatures of the tubular structure at a plurality of first points along the tubular structure are provided by the first providing unit 6. The first providing unit 6 thus provides the first distribution. These curvature values can be provided before, during or after instrument 4 has been introduced into the tubular structure of patient 3. After instrument 4 has been introduced into the tubular structure of patient 3, strain values indicative of extensions of instrument 4 at a plurality of second points along instrument 4 are provided by the second providing unit 6 in step 103. The second providing unit 7 thus provides the second distribution. In step 104, the position of instrument 4 within the tubular structure is determined by position determining unit 8 on the basis of the first and second distributions, and in step 105, a visualisation of the tubular structure is generated by visualisation generating unit 11 on the basis of the image provided and the position determined, the generated visualisation being displayed in step 106 on output unit 13. Steps 102-104 can be viewed as steps of a position determining method for determining a position of an instrument within a tubular structure.

The position determining device described above allows endotubular navigation based on strain profiles, which are determined, for example, by means of fibre-optic strain sensors that can be integrated in a medical instrument such as a catheter, a guide wire, a bronchoscope or some other medical instrument.

The position determining device described and also the position determining method are preferably adapted in such a way that they allow real-time correlation of strain measurement with a given tube-like structure, that is, the tubular structure. The tubular structure is preferably extracted from pre-interventional image data, with a scalar curvature profile of the medical instrument being determined on the basis of the extracted tubular structure for each possible path through the tubular structure. This can be done, for example, by extracting the respective blood vessel centre line, or a biophysical simulation of the anticipated instrument position in the blood vessel. This plurality of curvature profiles for a plurality of paths are then provided as first distributions to the intra-interventional mapping step.

During the intervention, the strain profile of the medical instruments, i.e. the second distribution, is determined and correlated with the previously determined curvature profiles, i.e. the first distributions. Measures of distance, i.e. dissimilarity measures, between the strain profile and the respective curvature profile are preferably selected such that the non-linear relationship between curvature and strain is taken into account.

If a strain profile along the medical instrument is used as the second distribution, it is not necessary to determine a curvature profile on the basis of at least two strain profiles, in order to determine, on the basis of the curvature profile, a three-dimensional shape of the medical instrument, for example, which could then be mapped onto the tubular structure. A single optical fibre or a single optical fibre core with strain sensors is sufficient, therefore, to determine the position of the medical instrument, is relatively inexpensive to produce and can also be integrated relatively easily into a medical instrument.

Figure 3:
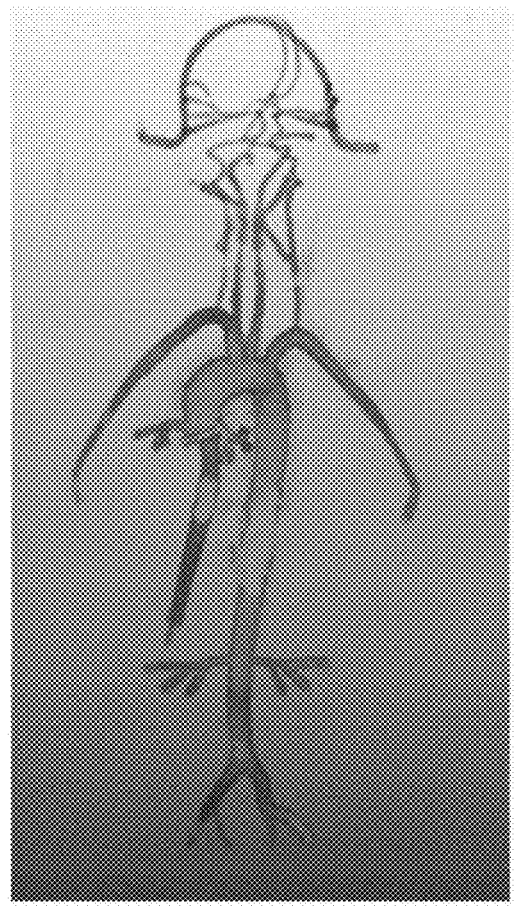
FIG. 3 shows an image of a tubular structure.
Figure 4:
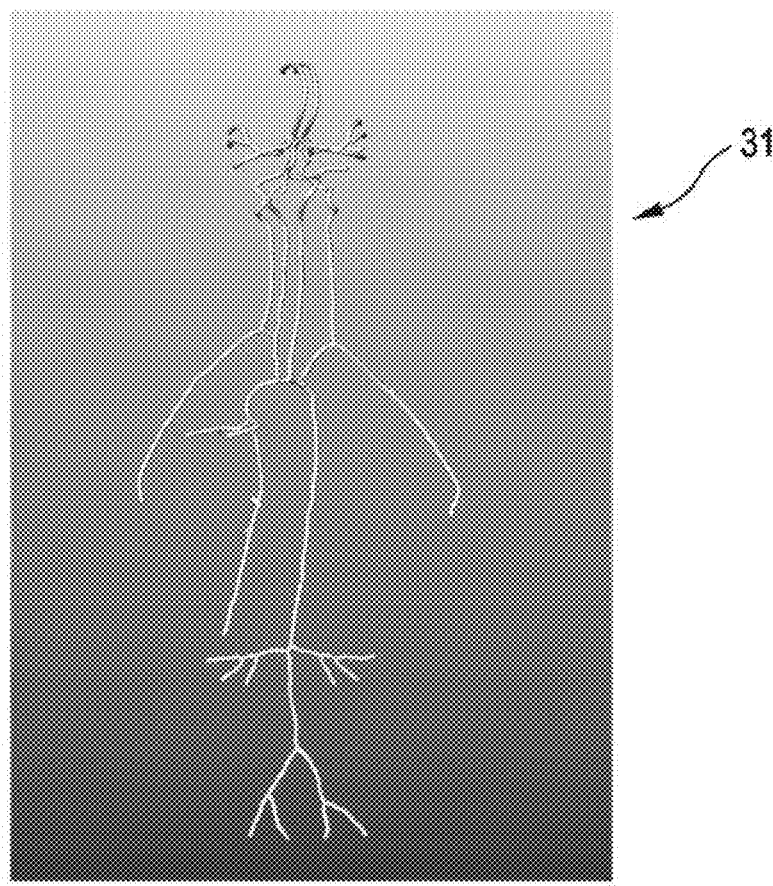
FIG. 4 shows a vascular graph representing the tubular structure and from which the image shown in FIG. 3 was derived.

FIG. 3 shows an example of a three-dimensional image of a tubular structure, and FIG. 4 illustrates a vascular graph 31, which was generated on the basis of the image shown in FIG. 3 and which represents the tubular structure. Vascular graph 31 and thus the tubular structure are branched and not cyclic.

Figure 5:
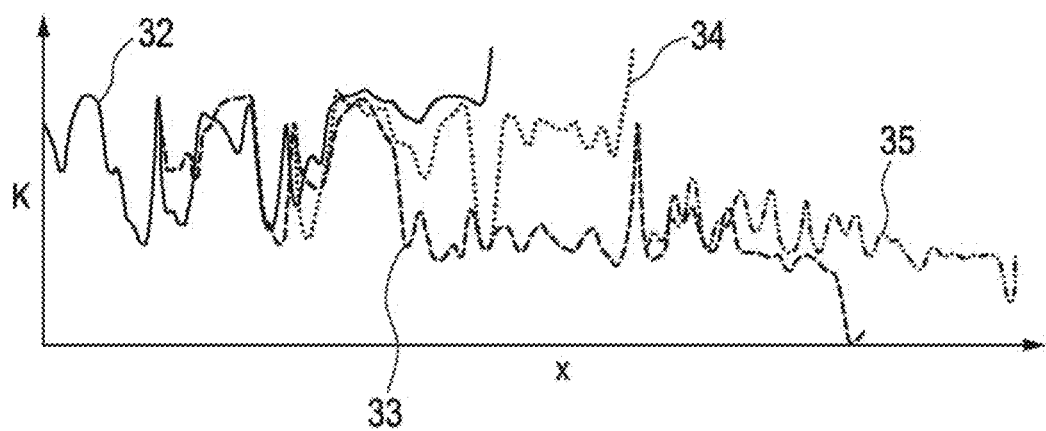
FIG. 5 shows different first distributions of curvature values for different paths within the tubular structure.

FIG. 5 shows four examples of curvature value profiles 32 ... 35 for four paths within the tubular structure, with the curvature K plotted along the vertical axis and the respective point along the respective path plotted along the horizontal axis. This means that, for each point along the corresponding path, a local curvature is calculated on the basis of the tubular structure, whereby the different paths, which can also be referred to as the vascular tree paths, are the result of branching within the tubular structure. The local curvature is preferably determined along all the vascular tree paths. FIG. 5 thus shows a plurality of first distributions.

The strain sensors arranged along the medical instrument are used to determine strain values at particular points, which may correlate with the curvature of the tubular structure. It should be noted here that, depending on the orientation of the optical fibres relative to the respective path, individual local strain sensors may not be affected by the curvature of the path. This is particularly the case when the curvature is orthogonal to the positional axis of the strain sensor in the medical instrument. The position of the medical instrument within the tubular structure can nevertheless be accurately determined by means of the position determining device and the position determining method.

Figure 6:
FIG. 6 shows a distribution of dissimilarity scores for different candidate positions and one path.

In a first step, position determining unit 8 preferably determines the most plausible position of the medical instrument for each possible vascular tree path. For each possible position of the medical instrument, i.e. for each candidate position along a vascular tree path, the curvature values along the respective first distribution of the respective vascular tree path and the measured strain values in the medical instrument are compared using a measure of distance, i.e. using a dissimilarity measure. Different measures of distance are conceivable, and for each possible distance measure or dissimilarity measure, characteristics are extracted from the curvature and strain profiles, i.e. from the first and second distributions, and a distance, i.e. a dissimilarity score, between the first and second distributions is determined for a specific candidate position on the basis of those characteristics. For each vascular tree path through the tubular structure, a plausibility, i.e. a dissimilarity score, is thus obtained at each possible position, i.e. of each candidate position of the medical instrument along the respective vascular tree path. FIG. 6 illustrates the plausibility or dissimilarity score in the form of different grey-scale values for different candidate positions p.

In one embodiment, the most plausible candidate position of the medical instrument in a particular vascular tree path can be thought of as the candidate position for which the lowest dissimilarity score has been determined, i.e. for which the smallest distance has been determined. However, due to noise, for example, determining a position in this way may involve errors, so knowledge about previous points in time is preferably integrated into the determination of the most plausible candidate positions. For each vascular tree path and for each point in time, therefore, a distribution of dissimilarity scores for different candidate positions of the medical instrument relative to the respective vascular tree path is preferably determined, and this results in a map that could also be called an energy map and which is illustrated in FIG. 7.

Figure 7:
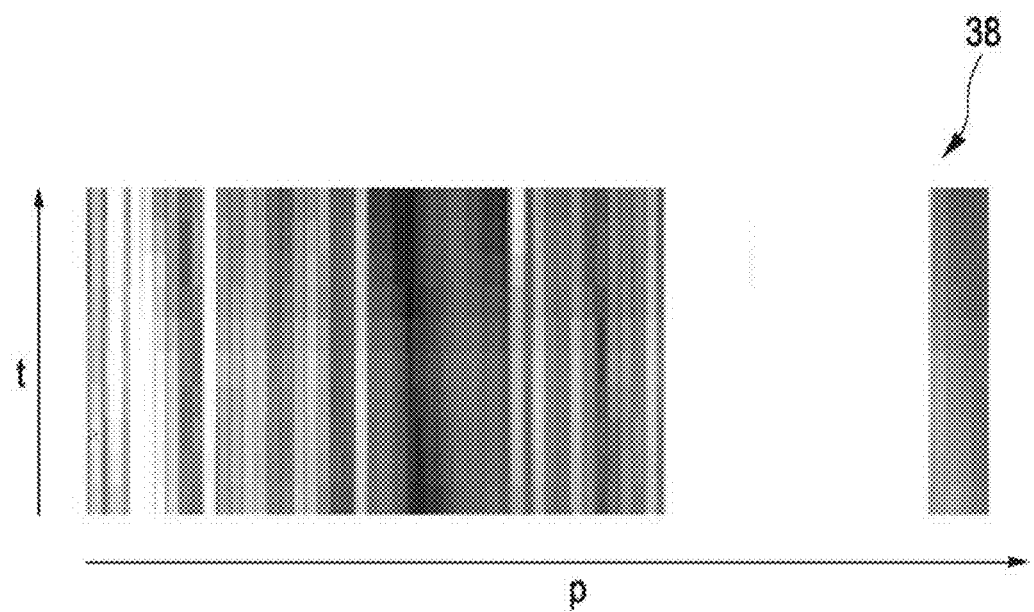
FIG. 7 shows dissimilarity scores for different candidate positions and times for a path within the tubular structure, said scores forming a map.
Figure 8:
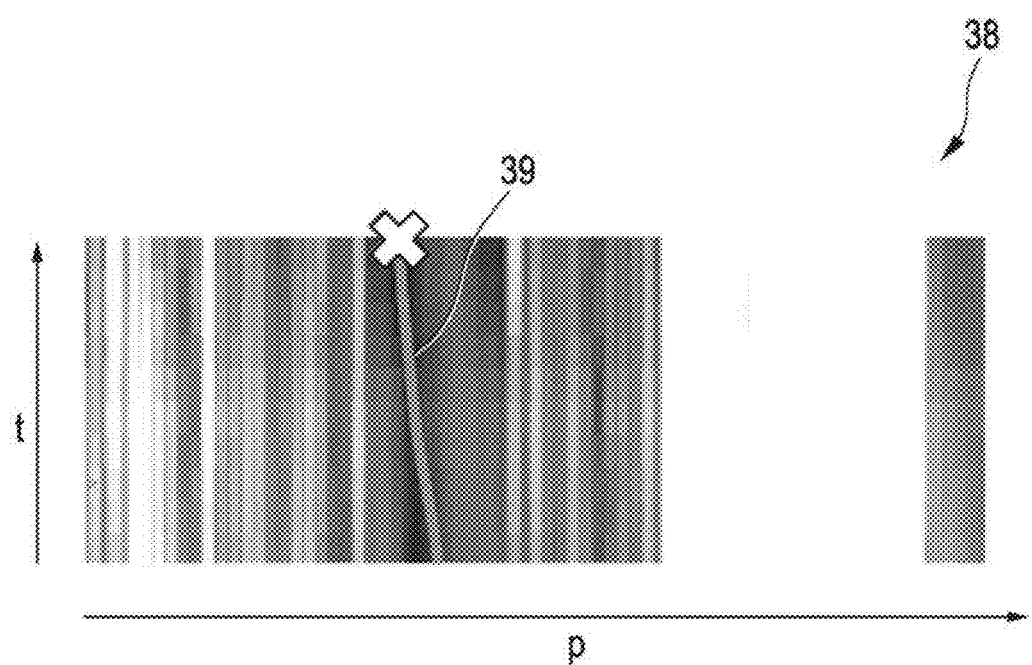
FIG. 8 shows an optimal route through the map shown in FIG. 7.

In FIG. 7, the different dissimilarity scores in energy map 38 are shown with different grey-scale values, with energy map 38 being plotted with different candidate positions p and different times t. That means that energy map 38 contains respective dissimilarity scores, shown in grey-scale form in FIG. 7, for different candidate positions p and different times t. The most plausible position of the medical instrument in a vascular tree path is preferably obtained then from an optimal route through energy map 38. Optimal preferably means that the accumulated dissimilarity score along the route through energy map 38 is minimal, optionally taking a regularity condition into account. The optional regulatory condition could take into account, for example, that the route through energy map 38 should be as short as possible. It could also be taken into account that the route through energy map 38 should be as straight as possible. Technically, each route through energy map 38 is associated with certain costs that result from the accumulated dissimilarity scores and the optional regularity. The route with the lowest costs is the optimal path that defines the position of the medical instrument for a vascular tree path and for different times. Such an optimal route 39 is shown in FIG. 8.

Figure 9:
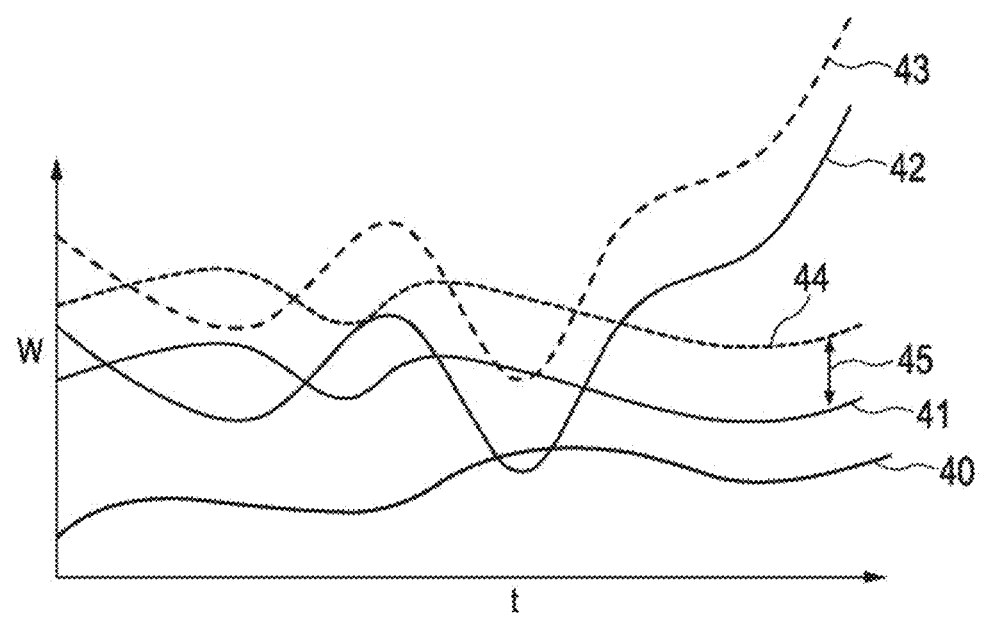
FIG. 9 shows different cost curves.

The position of the medical instrument in the overall tubular structure is now determined using the most plausible positions per vascular tree path. This is done by comparing the optimal energy map cost scores, i.e. the route scores of the optimal routes, of the individual vascular tree paths with each other. In one embodiment, the vascular tree path and the most plausible associated position with the lowest route score are selected. However, this approach is also noisy, so this can lead to errors in error detection, particularly since the finally determined position of the medical instrument can jump back and forth between vascular tree paths. To prevent this happening, a temporal regularisation that penalises jumps between vascular tree paths is preferred. To do this, changes in the optimal route score as a function of time per vascular tree path are stored, for example, as optimal cost curves (OCCs). Such OCCs 40 ... 42 are illustrated in FIG. 9. FIG. 9 illustrates OCCs 40 ... 42, which have different optimal route scores W for different times t.

The temporal regularisation is based on imposing a penalty term on all OCCs that were not minimal at a previous point in time. In FIG. 9, this penalty term is symbolised by double arrow 45. Curve 44 is based on OCC 41 after imposition of penalty term 45, and curve 43 is based on OCC 42, again after imposition of the penalty term. The penalty term is simply an additive value, preferably, which is predefined and can be determined in advance, for example when calibrating the system. The aforementioned thresholds and absolute value thresholds can be determined beforehand as part of a calibration. Thus, as described above, the position determining unit is preferably adapted to select at each point in time, from the calculated optimal routes, the optimal route for which a minimum route score has been determined, wherein the route score is increased, before the optimal route with the minimum route score is selected, for an optimal route for which no minimum route score was determined at earlier points in time compared to the route scores determined for the other optimal routes, The current determined position of the catheter within the tubular structure is marked by an X in FIG. 8.

Although different dissimilarity measures are described separately in the above embodiments, it is also possible to use combinations of these dissimilarity measures. For example, two or more dissimilarity measures can be linearly combined, and the linear combination that results can then be used for determining the position.

Although scalar strain values are measured along the medical instrument in the above embodiments in order to determine the second distribution, it is also possible in other embodiments to determine a plurality of strain values at the respective points along the medical instrument. That means that the strain can also be determined in at least two directions at the respective point along the medical instrument. The position can then be determined on the basis of these multi-component strain values and the first distribution of curvature values. In another embodiment, furthermore, the second distribution, too, can be a distribution of curvature values, so the position of the medical instrument within the tubular structure is determined on the basis of first and second distributions of curvature values. The second distribution of curvature values can also be determined on the basis of the aforementioned two-component or multi-component strain values. When the position of the medical instrument within the tubular structure is determined on the basis of first and second distributions of curvature values, the curvature values of both distributions are preferably scalar.

Other variations of the disclosed embodiments can be understood and carried out by those skilled in the art by implementing the claimed invention after studying the drawings, the description and the attached claims.

In the claims, the word "comprising" does not exclude other elements or steps, and the indefinite article "a" or "an" does not exclude a plurality.

A single apparatus or device may perform the functions of several objects specified in the claims. The mere fact that certain measures are mentioned in different dependent claims does not stipulate that a combination of those measures cannot be used to advantage.

Methods performed by one or more apparatuses or devices, such as determining the position of the instrument within the tubular structure, determining dissimilarity measure, determining route scores, etc., can also be carried out by any other number of apparatuses or devices. These methods and/or control of the imaging system according to the imaging method and/or control of the position determining device according to the position determining method can be carried out as program code means of a computer program and/or as dedicated hardware.

A computer program may be stored/provided on a suitable medium, for example on an optical storage medium or solid-state medium provided in combination with or as part of other hardware, but it may also be provided in other forms, for example via the Internet or other wired or wireless telecommunication systems.

None of the reference signs in the claims should be interpreted as limiting the scope of the invention.

The invention claimed is:

1. A position determining device for determining a current position of an elongate medical instrument within a tubular structure as the elongate medical instrument is moving, wherein the elongate medical instrument comprises a catheter, a bronchoscope, or a guide wire, said position determining device comprising:
    a first providing unit configured to provide a plurality of first distributions of curvature values for a plurality of paths within the tubular structure, wherein the first providing unit is a storage medium configured to store previously computed values that are the plurality of first distributions of curvature values, is a computer processor configured to execute code that receives the plurality of first distributions of curvature values, or is a computer processor configured to execute code to calculate the plurality of first distributions of curvature values;
    a second providing unit configured to provide a plurality of second distributions of strain values or curvature values, wherein the second providing unit is a storage medium configured to store previously computed values that are the plurality of second distributions of strain values or curvature values, is a computer processor configured to execute code that receives the plurality of second distributions of strain values or curvature values, or is a computer processor configured to execute code to calculate the plurality of second distributions of strain values or curvature values, and wherein the second providing unit is configured to provide the plurality of second distributions along the elongate medical instrument for different points in time, wherein each of the plurality of second distributions corresponds to a position of the elongate medical instrument relative to a path at a point in time within the tubular structure; and
    a position determining unit comprising a computer processor configured to execute program code that determines a most plausible position of the elongate medical instrument within one of the plurality of paths on the basis of the provided first and second distributions;
    wherein the position determining unit is further configured to determine the most plausible position of the elongate medical instrument as the elongate medical instrument is moved within the tubular structure by:
        determining for each respective path of the plurality of paths and for each point in time for a plurality of points in time, a distribution of dissimilarity scores for different candidate positions of the elongate medical instrument relative to the respective path by applying a dissimilarity measure to a respective first distribution and a respective second distribution, wherein the dissimilarity measure is adapted to return a dissimilarity score indicative of a dissimilarity of the respective first distribution and the respective second distribution, and
        determining the most plausible position of the elongate medical instrument relative to one of the plurality of paths on the basis of the dissimilarity scores determined for each of the respective different paths, the different points in time and the different candidate positions by determining optimal routes of the elongate medical instrument relative to each of the plurality of paths using route scores based upon the dissimilarity scores and determining which of these optimal routes represents the most plausible position of the elongate medical instrument relative to the one of the plurality of paths, and wherein the position determining unit is configured to forward for further processing the most plausible position of the elongate medical instrument as the current position of the elongate medical instrument in one of the plurality of paths in the tubular structure.

2. The position determining device of claim 1, wherein the plurality of first distributions of curvature values are scalar distributions.

3. The position determining device of claim 1, wherein the plurality of second distributions are based upon optical signals from optical strain sensors arranged along the elongate medical instrument.

4. The position determining device of claim 1, wherein the dissimilarity scores determined for the different points in time of the plurality of points in time and the different candidate positions for each path of the plurality of paths represent a map, wherein each respective dissimilarity score value in the map corresponds to a different map location specified by the respective point in time and respective candidate position of the elongate medical instrument relative to a respective path, and wherein the determining optimal routes of the elongate medical instrument relative to each of the plurality of paths using route scores based upon the dissimilarity scores and determining which of these optimal routes represents the most plausible position of the elongate medical instrument relative to the one of the plurality of paths further comprises:

for each path of the plurality of paths, providing a route score associated with each route through the respective map for each path, each route ending at a candidate position of the elongate medical instrument for a latest point in time and beginning at a candidate position of the elongate medical instrument for an earlier point in time, the associated route score depending on the dissimilarity scores along the respective route;

determining, for each path of the plurality of paths, a respective optimal route through the respective map by determining a minimum route score for the path based upon the route scores associated with each route through the respective map ; and determining the most plausible position of the elongate medical instrument relative to one of the plurality of paths based on the determined optimal routes.

5. The position determining device of claim 4, wherein the position determining device is further configured to provide the route scores for each path of the plurality of paths by determining a sum of the dissimilarity scores along each route through each respective map of each path of the plurality of paths.

6. The position determining device of claim 4, wherein the determining, for each path of the plurality of paths, the respective optimal route through the respective map and the determining the most plausible position of the elongate medical instrument relative to the one of the plurality of paths based on the determined optimal routes further comprises:

calculating the optimal routes for a respective path of the plurality of paths at different points in time such that a respective optimal route with a corresponding route score is determined based upon the dissimilarity scores calculated for a particular point in time and for earlier points in time and for the each of the candidate positions along the respective path;

selecting at each point in time, from the calculated optimal routes, the optimal route for which the minimum route score has been determined; and specifying the candidate positions defined by the selected optimal route as the position of the elongate medical instrument relative to one of the paths.

7. The position determining device of claim 1, wherein the position determining unit is configured to apply the dissimilarity measure by:

determining a spatial first gradient distribution for each of the plurality of first distributions of curvature values;

determining a spatial second gradient distribution for each of the plurality of second distributions of strain values or curvature values;

comparing, for each location along the elongate medical instrument, a respective spatial second gradient distribution with a respective spatial first gradient distribution, wherein each respective candidate position of the candidate positions defines which respective gradient of the spatial second gradient distribution is compared with which respective gradient of the spatial first gradient distribution at a respective location, wherein the position determining unit is further configured for the respective location and for the respective candidate position, to apply a sub-dissimilarity measure which is dependent a) on the directions of the respective gradient of the spatial second gradient distribution relative to the respective gradient of the spatial first gradient distribution or b) on the amount of the respective gradient of the spatial first gradient distribution and the amount of the respective gradient of the spatial second gradient distribution, and to determine a sub-dissimilarity score for each respective location by applying the sub-dissimilarity measure; and summing the sub-dissimilarity scores determined for each candidate position, in order to determine a respective dissimilarity score for the respective candidate position.

8. The position determining device of claim 1, wherein the position determining unit is configured to apply the dissimilarity measure to the respective first distribution and the respective second distribution by:

determining local maxima of the respective first distribution;

determining local maxima of the respective second distribution;

assigning to each local maximum of the respective first distribution a local maximum of the respective second distribution, so that a sum of all the spatial distances between assigned local maxima is minimal, wherein each local maximum of the respective second distribution is assigned to only one local maximum of the respective first distribution; and adding the spatial distances between the assigned local maxima of the respective first distribution and the assigned local maxima of the second respective distribution.

9. The position determining device of claim 1, wherein the position determining unit is configured to apply the dissimilarity measure to the respective first distribution and the respective second distribution by:

comparing a respective value of the respective second distribution with a respective value of the respective first distribution for each location along the elongate medical instrument, wherein the respective candidate position defines which respective value of the second distribution is compared with which respective value of the first distribution at a respective location, wherein, for the respective location and for the respective candidate position, the position determining unit is configured to use a sub-dissimilarity measure which is zero if a) the respective value of the respective first distribution is above a predefined first threshold or b) the respective value of the respective first distribution is below the first threshold and the respective value of the respective second distribution is below a predefined second threshold, and which otherwise has a positive value; and summing the sub-dissimilarity scores determined for a candidate position, in order to determine a respective dissimilarity score for the respective candidate position.

10. The position determining device of claim 1, wherein the position determining unit is configured to apply the dissimilarity measure to the respective first distribution and the respective second distribution by applying a normalised cross-correlation to the respective first distribution and the respective second distribution for the respective candidate position.

11. The position determining device of claim 1, wherein the plurality of second distributions of strain values or curvature values comprises strain values.

12. An imaging system, comprising:
a position determining device structured to determine the current position of an elongate medical instrument within a tubular structure in accordance with claim 1;
an imaging unit structured to provide an image of the tubular structure, wherein the imaging unit is a device configured to provide a computed tomography image, a magnetic resonance imaging image, or an other type of three-dimensional image; and
a visualisation generating unit comprising a computer processor configured to execute code that receives the forwarded current position of the elongate medical instrument in one of the plurality of paths and generates a visualisation of the tubular structure on the basis of the image provided and the position determined, showing the current position of the elongate medical instrument in a respective path in the tubular structure based upon the most plausible position determined from the distributions of dissimilarity scores.

13. An imaging method, comprising:
determining an image of a tubular structure;
determining the current position of an elongate medical instrument within the tubular structure using a position determining device configured according to claim 1; and
generating a visualisation of the tubular structure on the basis of the image provided and the position determined, showing the current position of the elongate medical instrument in a respective path in the tubular structure based upon the most plausible position determined from the distributions of dissimilarity scores.

14. A non-transitory computer-readable storage medium containing instructions that, when executed, cause a computer processor of an imaging system to provide an image of a tubular structure and to generate a visualisation of the tubular structure on a basis of the image provided and a current position, by performing a method comprising:
receiving the image of the tubular structure from an imaging device configured to provide a computed tomography image, a magnetic resonance imaging image, or an other type of three-dimensional image;
determining the current position of an elongate medical instrument within the tubular structure using a position determining device configured in accordance with claim 1; and
generating a visualisation of the tubular structure on the basis of the image provided and the position determined, showing the current position of the elongate medical instrument in a respective path in the tubular structure based upon the most plausible position determined from the distributions of dissimilarity scores.

15. A method for determining a current position of an elongate medical instrument within a tubular structure as the elongate medical instrument is moving, wherein the elongate medical instrument comprises a catheter, a bronchoscope, or a guide wire, comprising:
under control of one or more computer processors,
determining, using stored values, received values, or calculated values, a plurality of first distributions of curvature values for a plurality of paths within the tubular structure;
determining, using stored values, received values, or calculated values, a plurality of second distributions of strain values or curvature values along the elongate medical instrument, wherein the plurality of second distributions are determined along the elongate medical instrument for different points in time, and wherein the plurality of second distributions correspond to a plurality of positions of the elongate medical instrument relative to a path within the tubular structure; and
calculating a most plausible position of the elongate medical instrument relative to one of the plurality of paths on the basis of the determined first distribution of curvature values and the determined second distribution of strain values or curvature values as the elongate medical instrument is moved within the tubular structure by:
determining, for each respective path of the plurality of paths and for each point in time for a plurality of points in time, a distribution of dissimilarity scores for different candidate positions of the elongate medical instrument relative to the respective path by applying a dissimilarity measure to a respective first distribution and a respective second distribution, wherein the dissimilarity measure is adapted to return a dissimilarity score indicative of a dissimilarity of the respective first distribution and the respective second distribution;
determining the most plausible position of the elongate medical instrument relative to one of the paths on the basis of the dissimilarity scores determined for each of the plurality of paths, the different points in time and the different candidate positions by determining optimal routes of the elongate medical instrument relative to each of the plurality of paths using route scores based upon the dissimilarity scores and determining which of these optimal routes represents the most plausible position of the elongate medical instrument relative to the one of the plurality of paths; and
forwarding for further processing the most plausible position of the elongate medical instrument as the determined current position of the elongate medical instrument in one of the plurality of paths in the tubular structure.

16. A non-transitory computer-readable storage medium containing instructions for controlling a computer processor to determine a current position of an elongate medical instrument within a tubular structure as the elongate medical instrument is moving, wherein the elongate medical instrument comprises a catheter, a bronchoscope, or a guide wire, by performing on a position determining device a method comprising:

determining a plurality of first distributions of curvature values for each of a plurality of paths within the tubular structure;

determining a plurality of second distributions of strain values or curvature values along the elongate medical instrument, wherein the plurality of second distributions are determined along the elongate medical instrument for different points in time, and wherein the plurality of second distributions correspond to a plurality of positions of the elongate medical instrument relative to a path within the tubular structure; and calculating a most plausible position of the elongate medical instrument relative to one of the plurality of paths on the basis of the determined first distribution of curvature values and the determined second distribution of strain values or curvature values as the elongate medical instrument is moved within the tubular structure;

determining, for each respective path of the plurality of paths and for each point in time for a plurality of points in time, a distribution of dissimilarity scores for different candidate positions of the elongate medical instrument relative to the respective path by applying a dissimilarity measure to a respective first distribution and a respective second distribution, wherein the dissimilarity measure is adapted to return a dissimilarity score indicative of a dissimilarity of the respective first distribution and the respective second distribution;

determining the most plausible position of the elongate medical instrument relative to one of the paths on the basis of the dissimilarity scores determined for each of the plurality of paths, the different points in time and the different candidate positions by determining optimal routes of the elongate medical instrument relative to each of the plurality of paths using route scores based upon the dissimilarity scores and determining which of these optimal routes reflects the most plausible position of the elongate medical instrument relative to the one of the plurality of paths; and forwarding for further processing the most plausible position of the elongate medical instrument as the determined current position of the elongate medical instrument in one of the plurality of paths in the tubular structure.

\* \* \* \* \*